(12) United States Patent
Zeiner et al.

(10) Patent No.: US 7,862,581 B2
(45) Date of Patent: Jan. 4, 2011

(54) TISSUE CONVEYOR FOR USE IN GASTRIC REDUCTION SURGERY AND ASSOCIATED METHOD FOR USE

(75) Inventors: Mark S. Zeiner, Mason, OH (US); Michael J. Stokes, Cincinnati, OH (US); Jason L. Harris, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 455 days.

(21) Appl. No.: 12/113,765

(22) Filed: May 1, 2008

(65) Prior Publication Data
US 2009/0275977 A1 Nov. 5, 2009

(51) Int. Cl.
*A61B 17/08* (2006.01)
(52) U.S. Cl. .................................................... 606/207
(58) Field of Classification Search ......... 606/117–122, 606/160–162, 205–210
See application file for complete search history.

(56) References Cited

U.S. PATENT DOCUMENTS

| 5,713,896 | A * | 2/1998 | Nardella .............. 606/50 |
| 6,269,819 | B1 | 8/2001 | Oz |
| 6,478,791 | B1 | 11/2002 | Carter |
| 6,558,400 | B2 | 5/2003 | Deem et al. |
| 7,717,926 | B2 * | 5/2010 | Whitfield et al. ............ 606/143 |
| 2004/0225305 | A1 | 11/2004 | Ewers |
| 2005/0267529 | A1 | 12/2005 | Crockett |
| 2007/0197858 | A1 | 8/2007 | Goldfarb |

FOREIGN PATENT DOCUMENTS

EP 1187559 3/2002

* cited by examiner

*Primary Examiner*—Kevin T Truong
(74) *Attorney, Agent, or Firm*—Welsh Flaxman & Gitler LLC

(57) ABSTRACT

A tissue conveyor includes a conveyor body having a proximal end and a distal end. The proximal end includes a handle allowing for operator control of an end effector located at the distal end. The end effector includes a grasper assembly composed of a first jaw bar and a second jaw bar connected by a support base to define a cavity into which tissue is drawn. A first conveyor member is positioned upon the first jaw bar for movement along an internal surface of the first jaw bar and a second conveyor member is positioned upon the second jaw bar for movement along an internal surface of the second jaw bar. The method for creating a tissue fold includes positioning a tissue conveyor adjacent tissue, pushing the respective first jaw bar and the second jaw bar into the tissue in the area where a fold is desired, and pulling the first conveyor member and the second conveyor member proximally to draw the first and second conveyor members and tissue into a cavity defined by the first jaw bar and the second jaw bar to create a tissue fold.

10 Claims, 12 Drawing Sheets

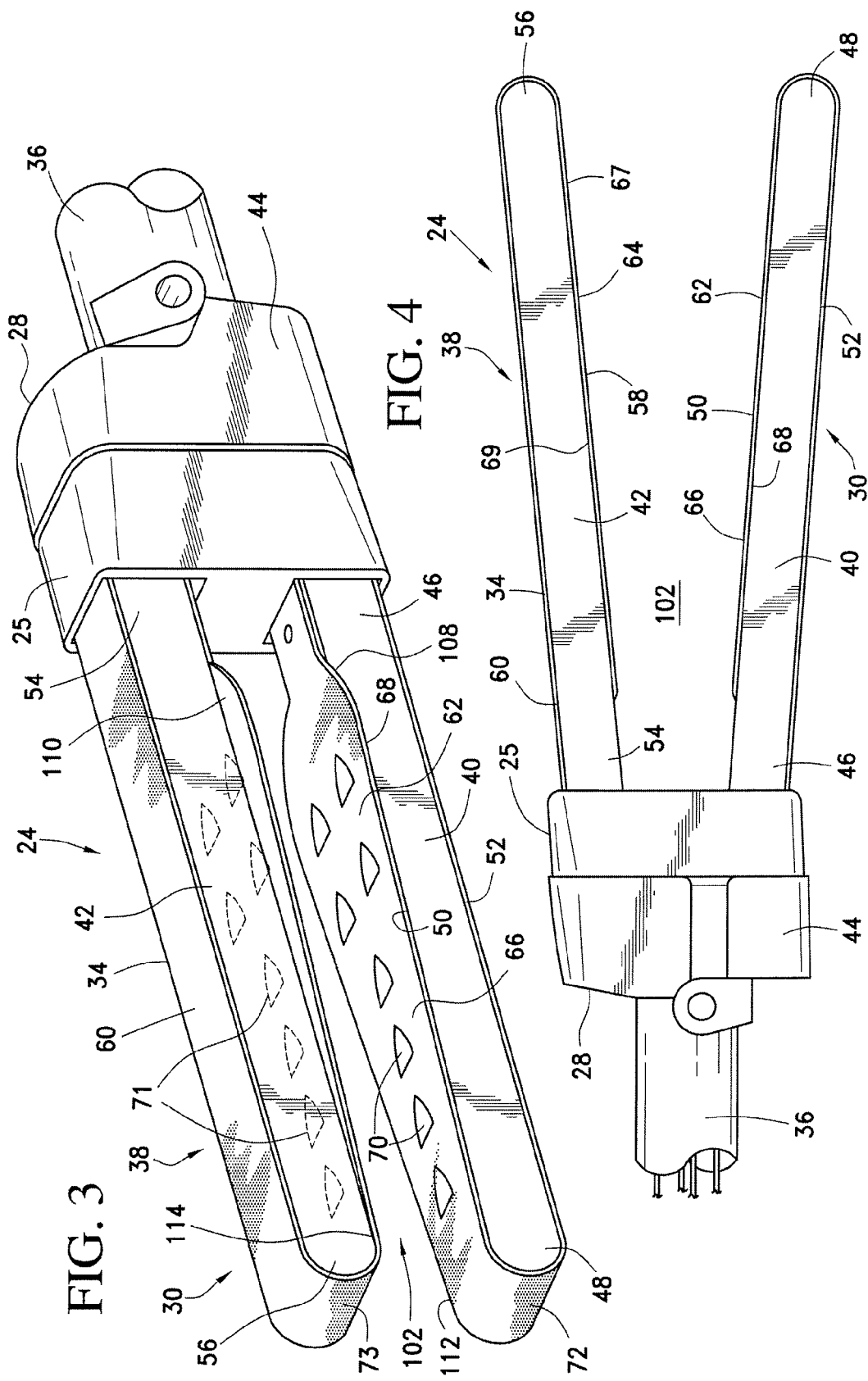

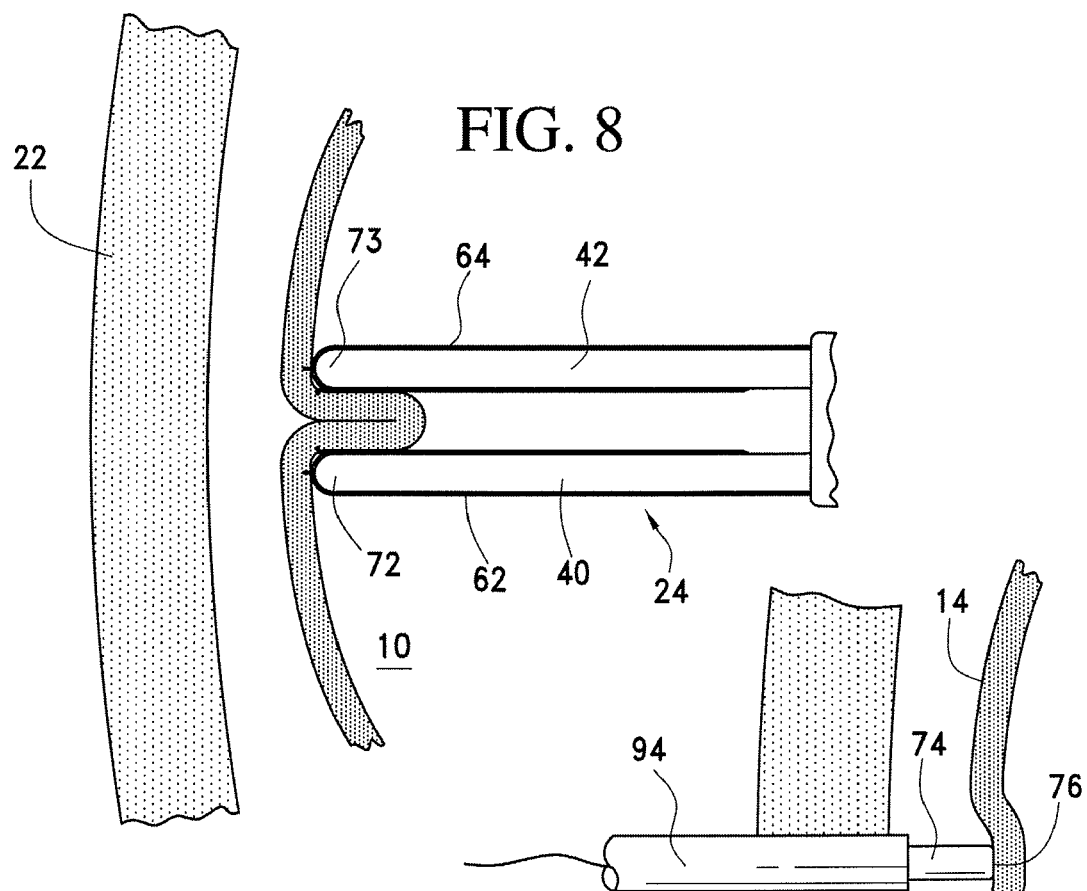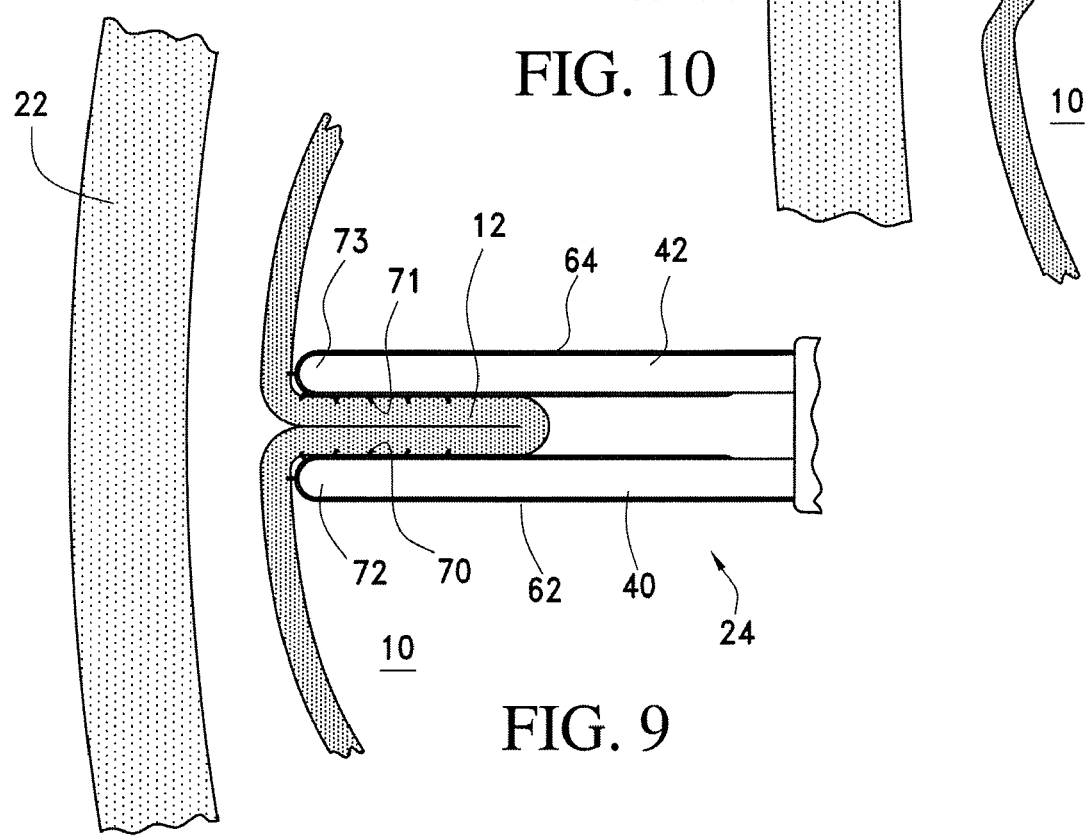

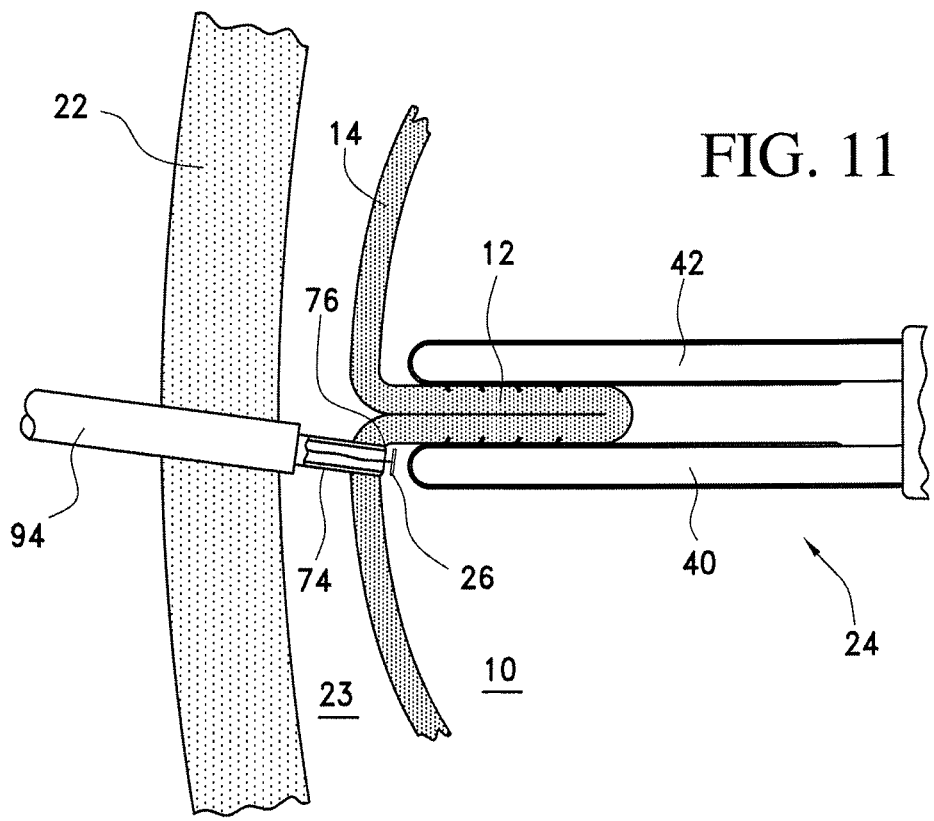
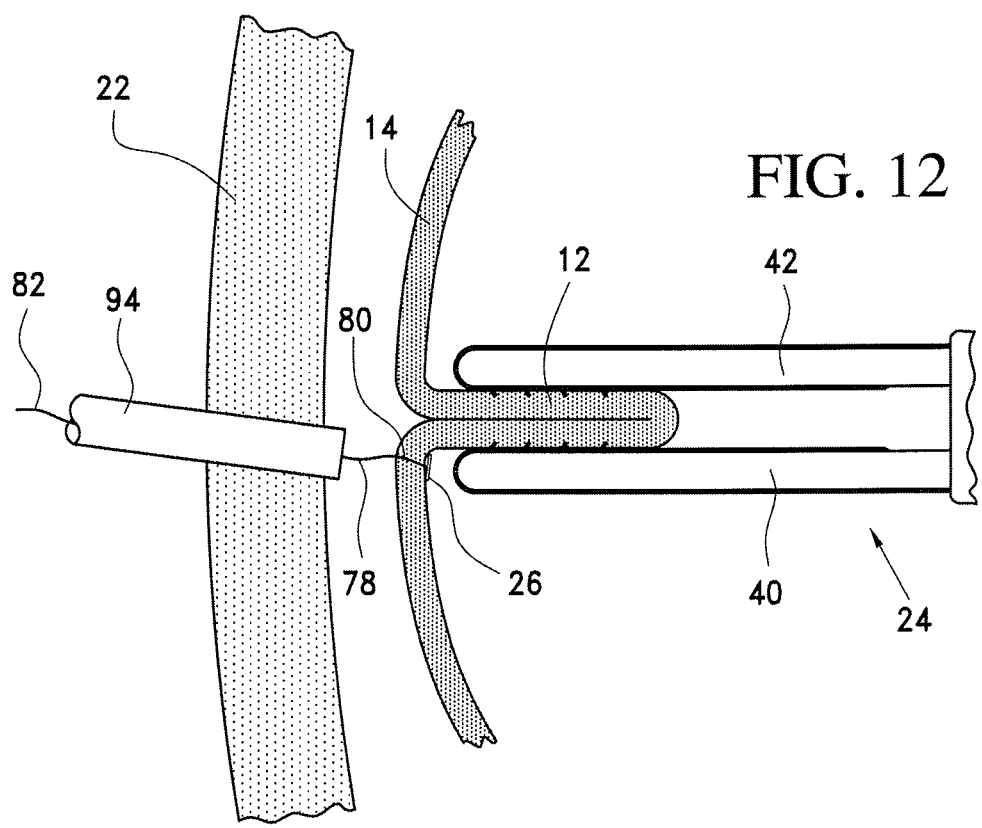

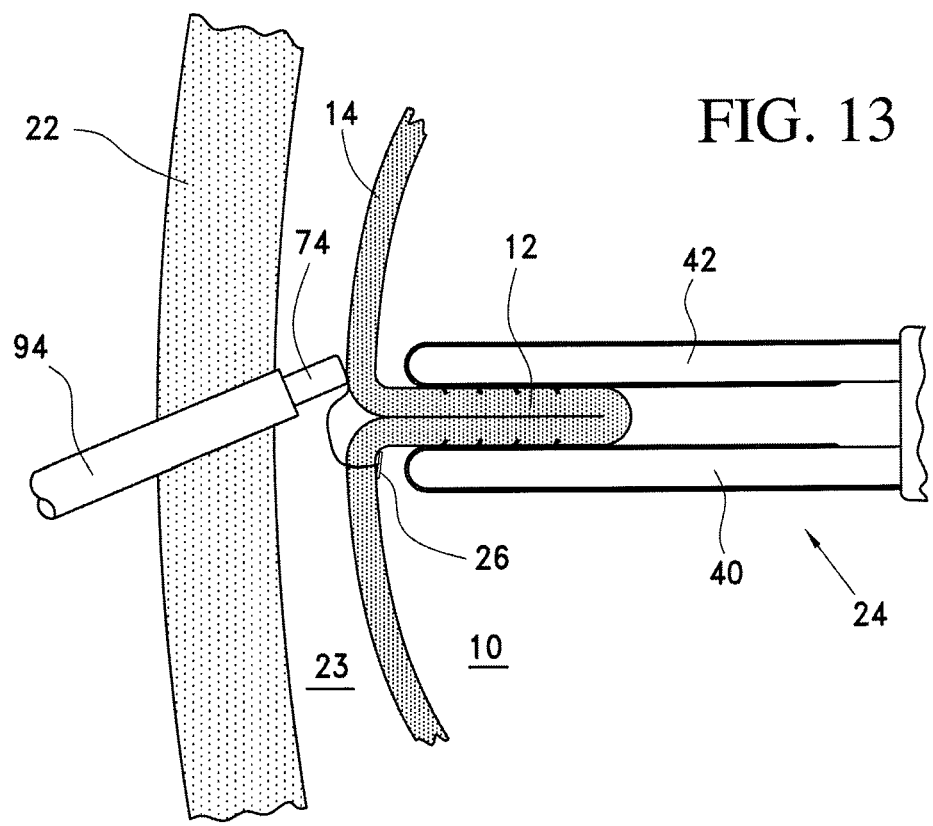
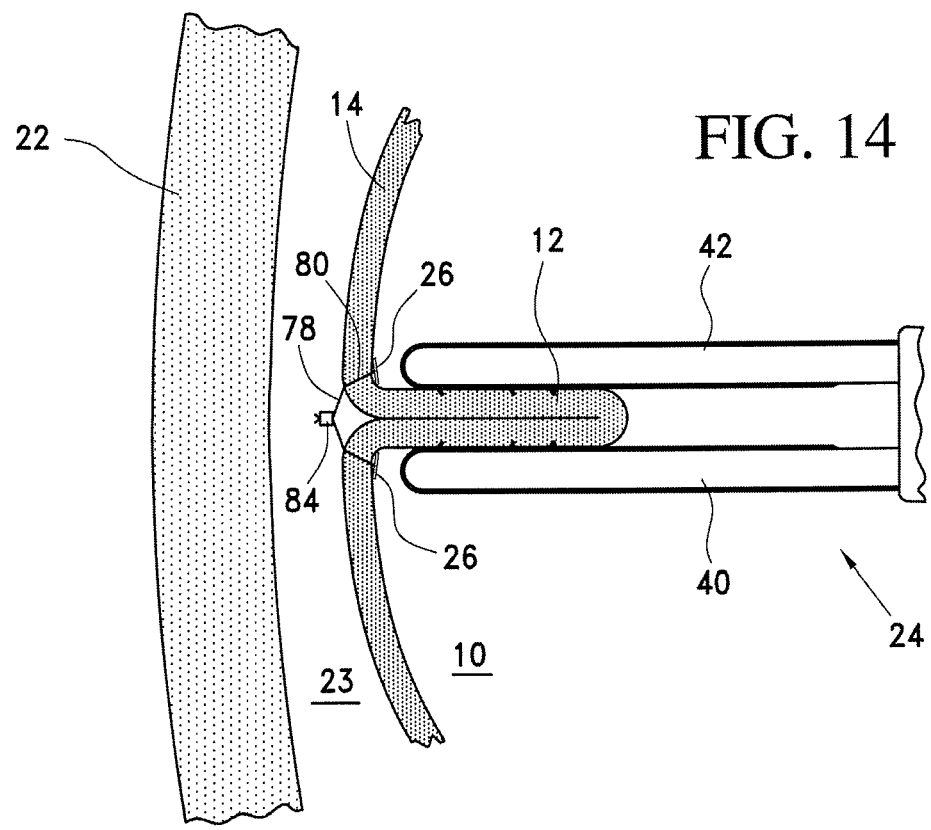

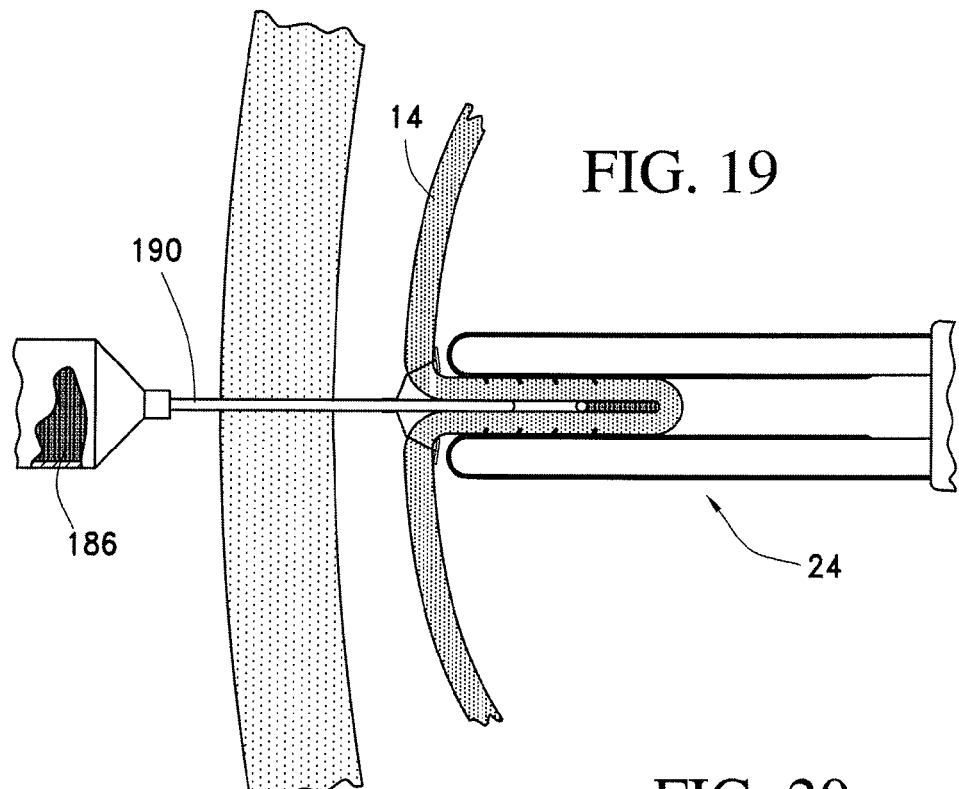
FIG. 19
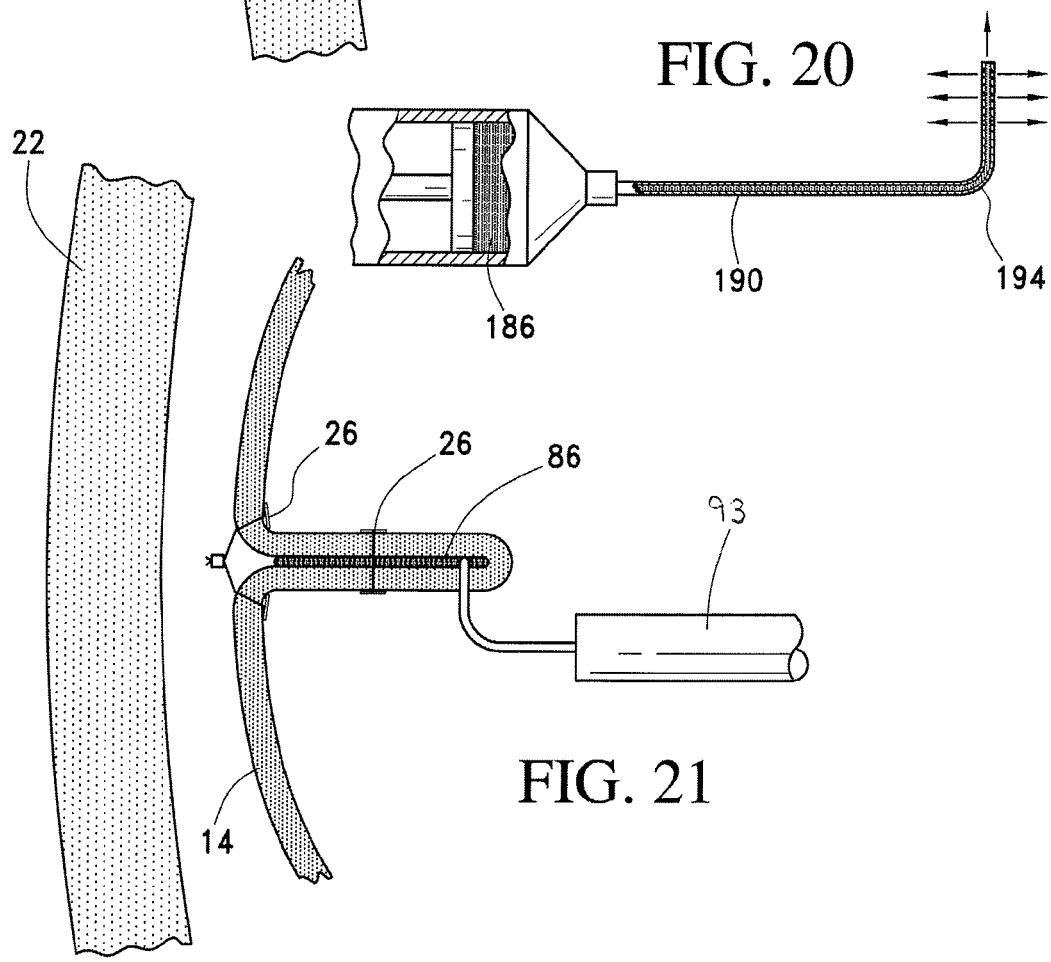
FIG. 20
FIG. 21

TISSUE CONVEYOR FOR USE IN GASTRIC REDUCTION SURGERY AND ASSOCIATED METHOD FOR USE

BACKGROUND OF THE INVENTION

1. Field of the Invention

The invention relates to a method and apparatus for creating a serosa-to-serosa fold along the stomach wall.

2. Description of the Related Art

Obesity is a medical condition affecting more than 30% of the population in the United States. Obesity affects an individual's personal quality of life and contributes significantly to morbidity and mortality. Obese patients, i.e. individuals having a body mass index ("BMI") greater than 30, often have a high risk of associated health problems (e.g., diabetes, hypertension, and respiratory insufficiency), including early death. With this in mind, and as those skilled in the art will certainly appreciate, the monetary and physical costs associated with obesity are substantial. In fact, it is estimated the costs relating to obesity are in excess of 100 billion dollars in the United States alone. Studies have shown that conservative treatment with diet and exercise alone may be ineffective for reducing excess body weight in many patients. Bariatrics is the branch of medicine that deals with the control and treatment of obesity. A variety of surgical procedures have been developed within the bariatrics field to treat obesity. The most common currently performed procedure is the Roux-en-Y gastric bypass (RYGB). This procedure is highly complex and is commonly utilized to treat people exhibiting morbid obesity. In a RYGB procedure a small stomach pouch is separated from the remainder of the gastric cavity and attached to a resectioned portion of the small intestine. This resectioned portion of the small intestine is connected between the "smaller" gastric cavity and a distal section of small intestine allowing the passage of food therebetween. The conventional RYGB procedure requires a great deal of operative time. Because of the degree of invasiveness, post-operative recovery can be quite lengthy and painful. Still more than 100,000 RYGB procedures are performed annually in the United States alone, costing significant health care dollars.

In view of the highly invasive nature of the RYGB procedure, other less invasive procedures have been developed. These procedures include gastric banding, which constricts the stomach to form an hourglass shape. This procedure restricts the amount of food that passes from one section of the stomach to the next, thereby inducing a feeling of satiety. A band is placed around the stomach near the junction of the stomach and esophagus. The small upper stomach pouch is filled quickly, and slowly empties through the narrow outlet to produce the feeling of satiety. Other forms of bariatric surgery that have been developed to treat obesity include Fobi pouch, bilio-pancreatic diversion and gastroplasty or "stomach stapling".

Morbid obesity is defined as being greater than 100 pounds over one's ideal body weight. For individuals in this category, RYGB, gastric banding or another of the more complex procedures may be the recommended course of treatment due to the significant health problems and mortality risks facing the individual. However, there is a growing segment of the population in the United States and elsewhere who are overweight without being considered morbidly obese. These persons may be 20-30 pounds overweight and want to lose the weight, but have not been able to succeed through diet and exercise alone. For these individuals, the risks associated with the RYGB or other complex procedures often outweigh the potential health benefits and costs. Accordingly, treatment options should involve a less invasive, lower cost solution for weight loss.

It is known to create cavity wall plications through endoscopic only procedures. However, operating solely within the interior of the gastric cavity limits the plication depth that can be achieved without cutting. Furthermore, access and visibility within the gastric and peritoneal cavities is limited in a purely endoscopic procedure as the extent of the reduction increases.

With the foregoing in mind, it is desirable to have a surgical weight loss procedure that is inexpensive, with few potential complications, and that provides patients with a weight loss benefit while buying time for the lifestyle changes necessary to maintain the weight loss. Further, it is desirable that the procedure be minimally invasive to the patient, allowing for a quick recovery and less scarring. The present invention provides such a procedure.

SUMMARY OF THE INVENTION

It is, therefore, an object of the present invention to provide a tissue conveyor including a conveyor body having a proximal end and a distal end. The proximal end includes a handle allowing for operator control of an end effector located at the distal end. The end effector includes a grasper assembly composed of a first jaw bar and a second jaw bar connected by a support base to define a cavity into which tissue is drawn. A first conveyor member is positioned upon the first jaw bar for movement along an internal surface of the first jaw bar and a second conveyor member is positioned upon the second jaw bar for movement along an internal surface of the second jaw bar.

It is also an object of the present invention to provide a tissue conveyor wherein the first jaw bar and the second jaw bar are pivotally secured to the support base of the end effector.

It is also an object of the present invention to provide a tissue conveyor wherein the first jaw bar pivots about an axis which is substantially parallel to an axis about which the second jaw bar pivots, while the axis about which the first jaw bar pivots and the axis about which the second jaw bar pivots are separated by a distance sufficient to permit the first jaw bar and the second jaw bar to grab and hold tissue therebetween.

It is a further object of the present invention to provide a tissue conveyor wherein the handle includes a lever connected to a linkage assembly for controlling pivotal movement of the first and second jaw bars.

It is also an object of the present invention to provide a tissue conveyor wherein the handle includes a control wheel actuating movement of first and second conveyor members for pulling tissue into a fold at the end effector.

It is another object of the present invention to provide a tissue conveyor wherein the first conveyor member includes an inner gripping surface and an outer surface, the inner gripping surface facing a cavity between the first jaw bar and the second jaw bar, and the second conveyor member includes an inner gripping surface and an outer surface, the inner gripping surface facing a cavity between the first jaw bar and the second jaw bar.

It is a further object of the present invention to provide a tissue conveyor wherein the first conveyor member includes a series of thin, v-shaped cutouts along its length and the second conveyor member includes a series of thin, v-shaped cutouts along its length.

It is also an object of the present invention to provide a tissue conveyor wherein each of the first conveyor member and the second conveyor member includes a first end and a second end, and the first conveyor member and the second conveyor member are connected to first and second string members wrapped about the end effector for actuation of the first conveyor member and the second conveyor members.

It is another object of the present invention to provide a tissue conveyor wherein the first and second string members are wrapped about the end effector for actuation of the first conveyor member and the second conveyor member in a manner creating simultaneous movement of the first conveyor member and second conveyor member.

It is a further object of the present invention to provide a tissue conveyor wherein passage of the first and second string members within the tissue conveyor is controlled by the inclusion of a series of pulleys positioned to facilitate movement of the of the first and second string members as they extend between the first and second conveyor members.

It is also an object of the present invention to provide a method for creating a tissue fold. The method is achieved by positioning a tissue conveyor adjacent tissue, wherein the tissue conveyor includes a conveyor body including a proximal end and a distal end, the proximal end includes a handle allowing for operator control of an end effector located at the distal end, the end effector includes a grasper assembly composed of a first jaw bar and a second jaw bar connected by a support base to define a cavity into which tissue is drawn, and a first conveyor member is positioned upon the first jaw bar for movement along an internal surface of the first jaw bar and a second conveyor member is positioned upon the second jaw bar for movement along an internal surface of the second jaw bar. The respective first jaw bar and the second jaw bar are pushed into the tissue in the area where a fold is desired. The first conveyor member and the second conveyor member are pulled proximally to draw the first and second conveyor members and tissue into a cavity defined by the first jaw bar and the second jaw bar to create a tissue fold.

It is another object of the present invention to provide a method including the step of applying a biosurgical adhesive for fastening the tissue fold.

Other objects and advantages of the present invention will become apparent from the following detailed description when viewed in conjunction with the accompanying drawings, which set forth certain embodiments of the invention.

BRIEF DESCRIPTION OF THE DRAWINGS

FIGS. 3 and 4 are respectively a perspective view and a side view of the present tissue conveyor.

FIGS. 8 to 16 show usage of the present tissue conveyor in the formation of a serosa-to-serosa fold.

FIGS. 19 and 20 show an alternate embodiment for the application of adhesive to a fold created in accordance with the present invention.

FIG. 21 shows another embodiment for the application of adhesive to a fold created in accordance with the present invention.

DESCRIPTION OF THE PREFERRED EMBODIMENT

Figure 1:
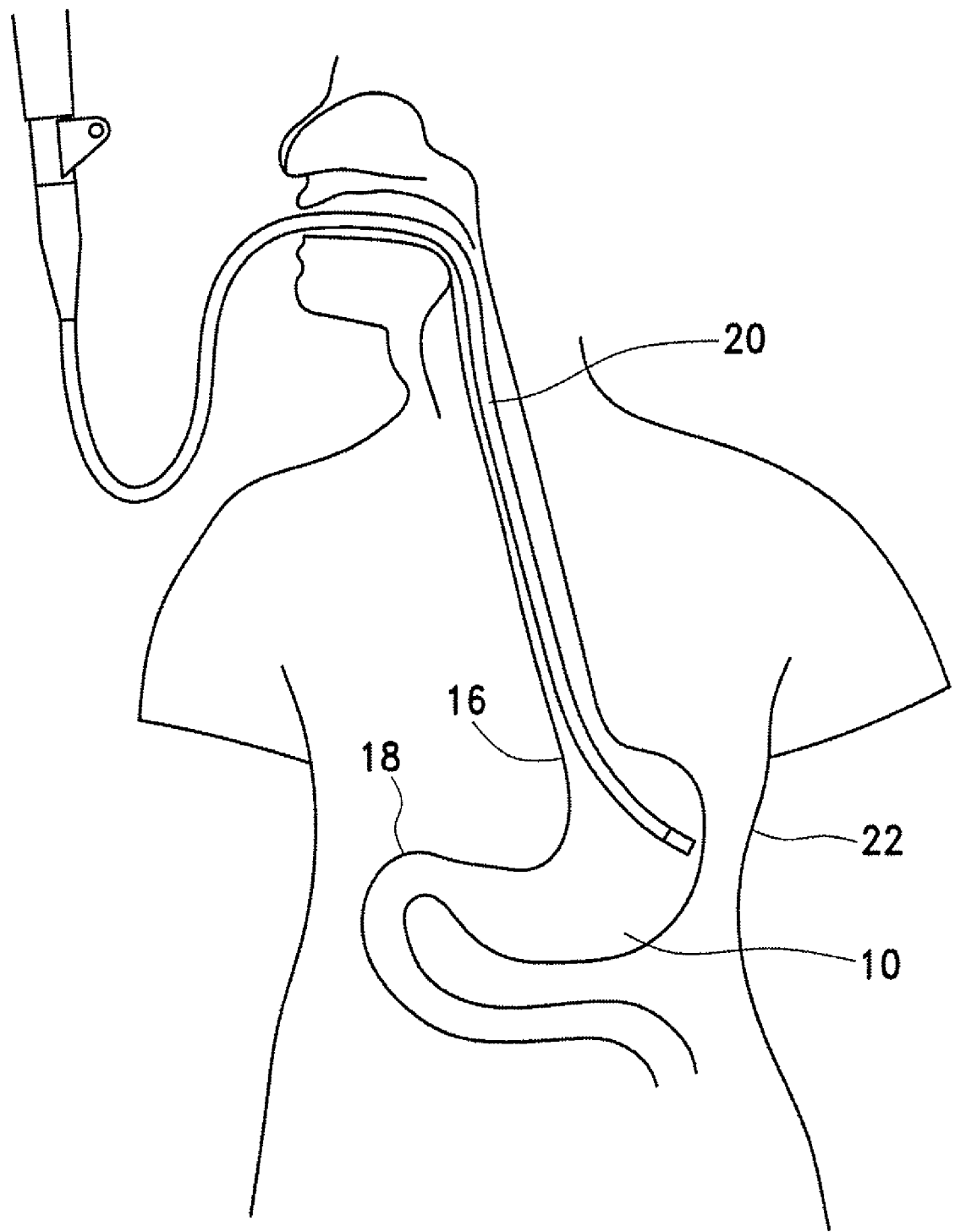
FIG. 1 is a schematic showing insertion of a gastroscope into the gastric cavity prior to gastric reduction surgery.
Figure 2:
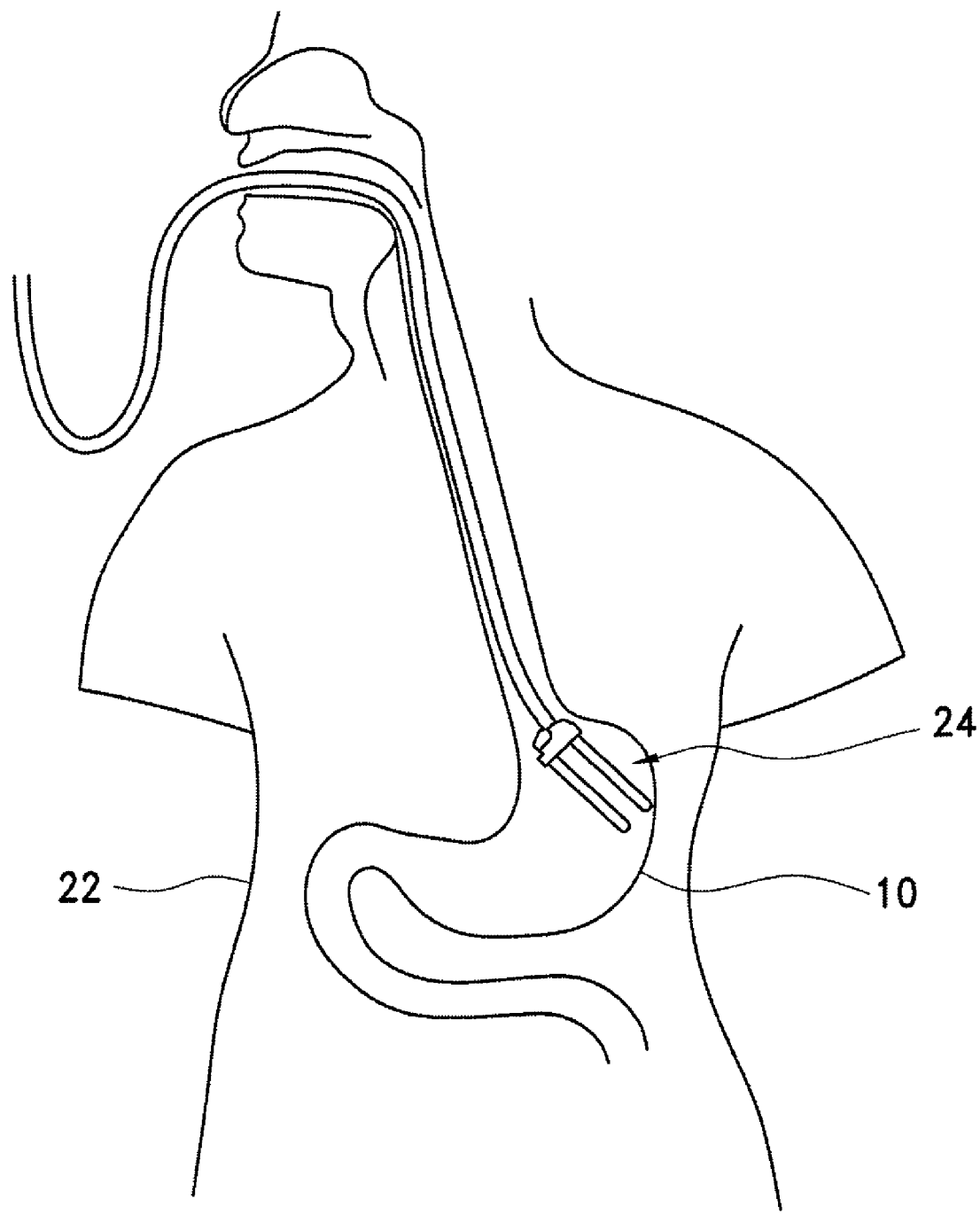
FIG. 2 is a schematic of the present tissue conveyor deployed within the gastric cavity.
Figure 5:
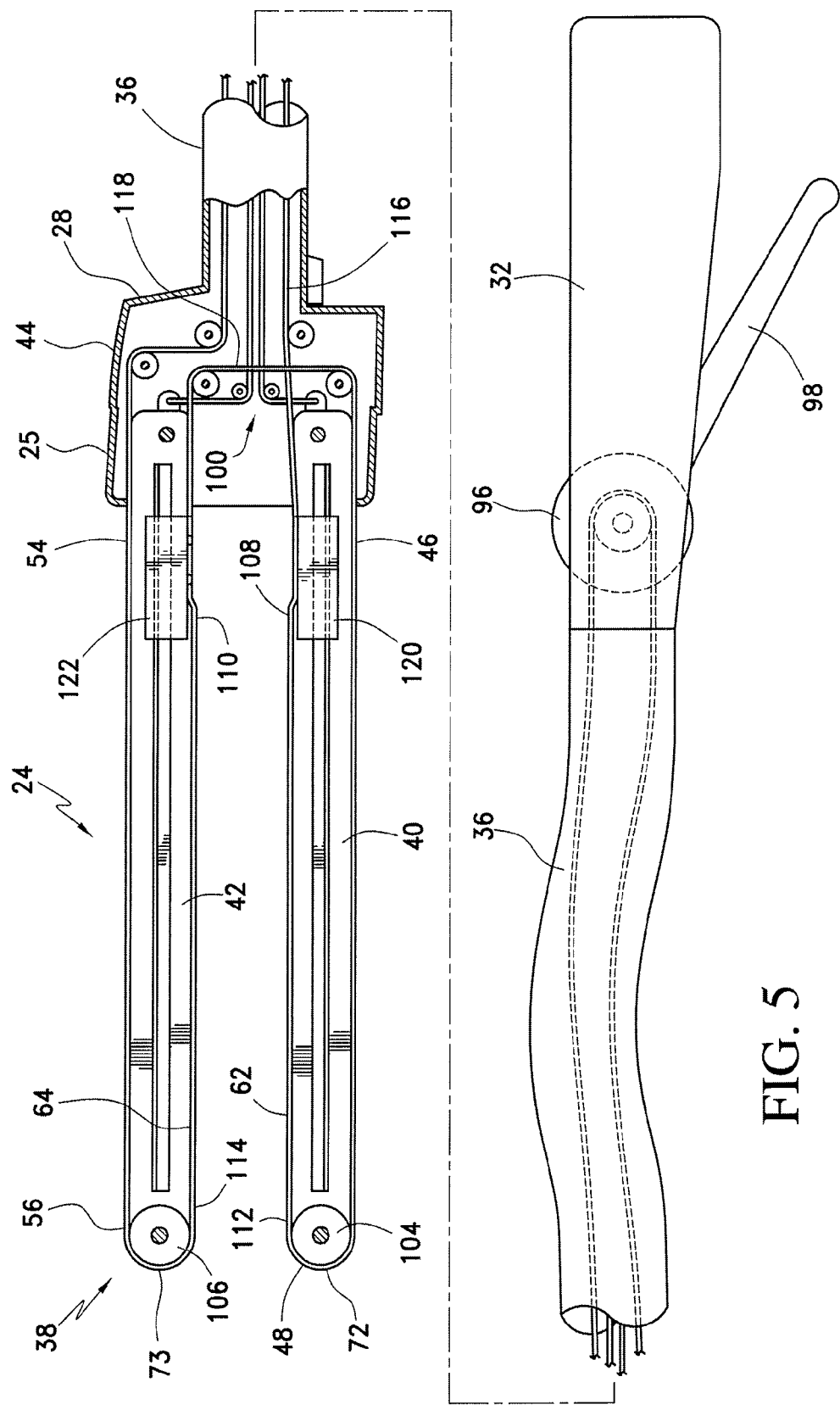
FIGS. 5 and 6 are partial cross sectional views of the present tissue conveyor showing operation thereof.
Figure 6:
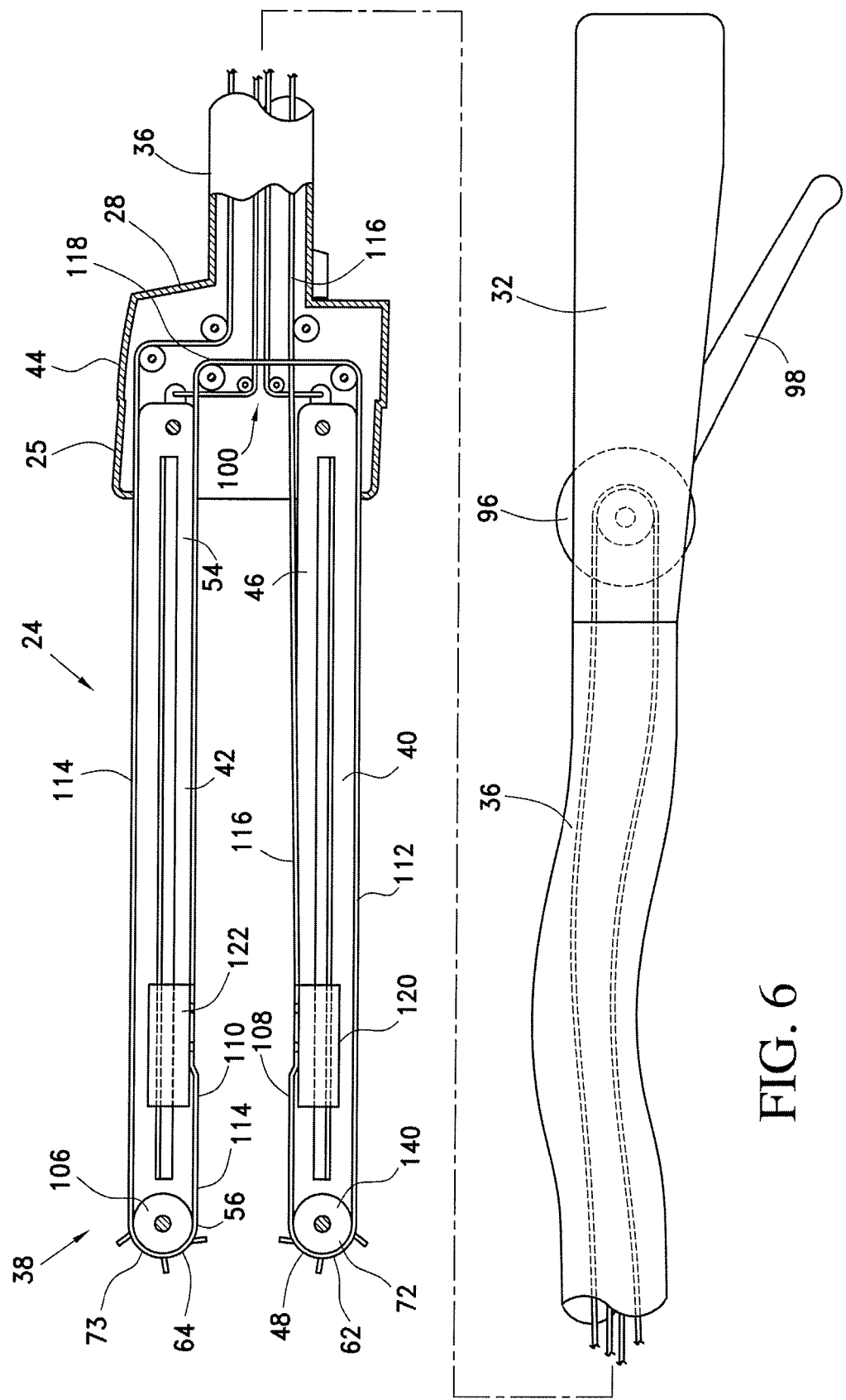
Figure 7:
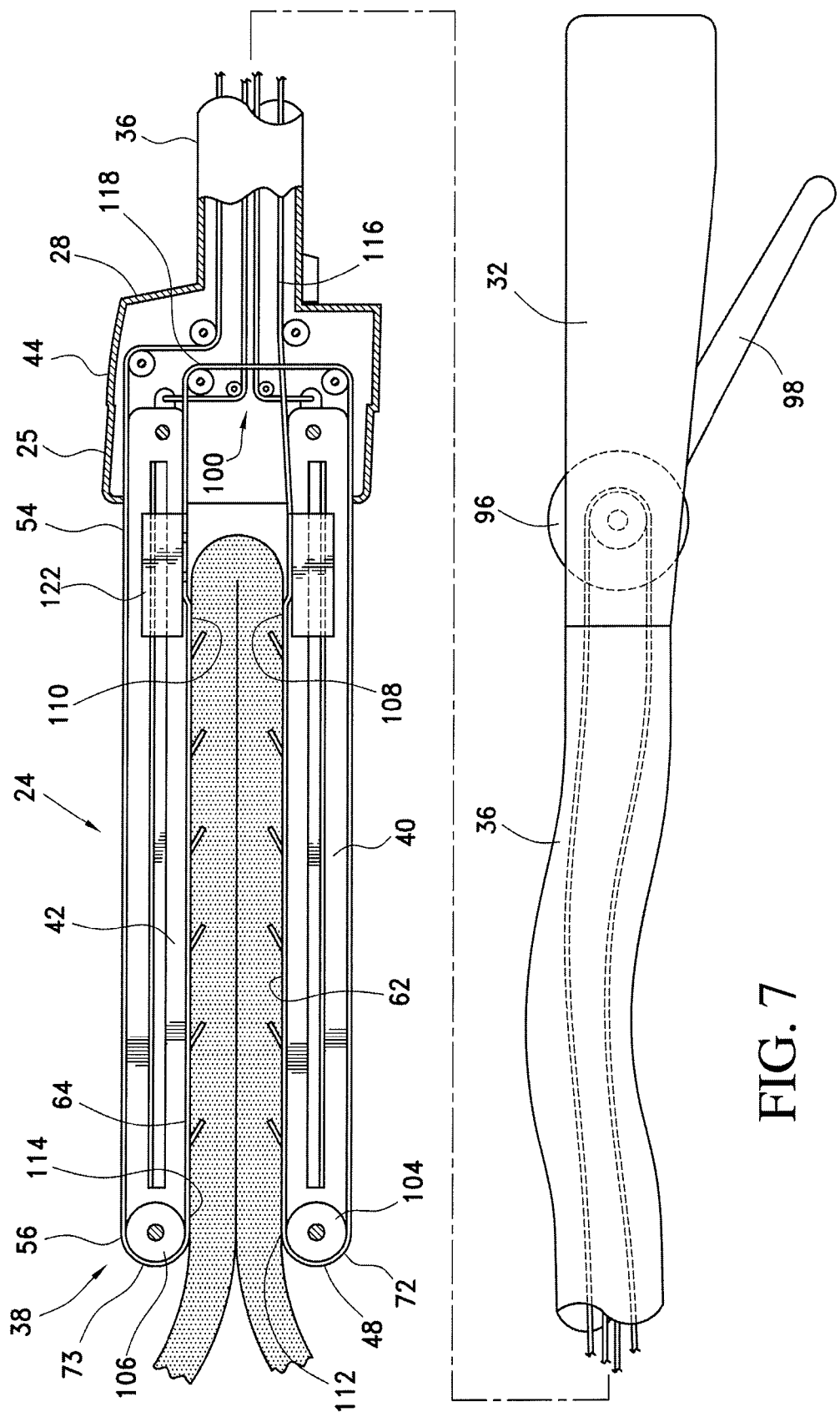
FIG. 7 is a partial cross sectional view of the tissue conveyor with tissue drawn therein.

The detailed embodiment of the present invention is disclosed herein. It should be understood, however, that the disclosed embodiment is merely exemplary of the invention, which may be embodied in various forms. Therefore, the details disclosed herein are not to be interpreted as limiting, but merely as a basis for teaching one skilled in the art how to make and/or use the invention.

With reference to the various figures, a method and apparatus for creating a serosa-to-serosa fold 12 from within the gastric cavity 10 for a transoral approach to gastric volume reduction in the treatment of morbid obesity is disclosed.

In accordance with the present invention, available stomach volume may be restricted by forming one or more folds 12 in the anterior wall 14 of the gastric cavity 10 (creating a serosa-to-serosa fold). The folds 12 reduce the outer surface area of the gastric cavity 10 and, correspondingly, the available food volume within the gastric cavity 10. In accordance with one restriction technique, available stomach volume is restricted by forming a single, longitudinally extending fold 12 along the anterior wall 14 of the gastric cavity 10. The fold 12 extends the full length of the anterior wall 14 of the gastric cavity 10 between the fundus 16 and the pylorus 18. Alternatively, a shorter fold may be formed depending upon the desired amount of gastric volume reduction.

Generally, to form a fold 12 in accordance with the present invention, a flexible gastroscope 20 is passed transesophageally into the gastric cavity 10 as shown in FIG. 1. The gastroscope 20 provides insufflation, illumination, and visualization of the gastric cavity 10, as well as a passageway into the gastric cavity 10 for the insertion and use of other endoscopic instruments. The gastric cavity 10 is first insufflated to create a sufficient rigid working surface along the gastric cavity 10 such that it may be pierced without damaging the opposing wall of the stomach. Insufflation of the gastric cavity 10 may also allow the boundaries of the gastric cavity 10 and the desired location for a fold 12 to be mapped out by external palpation. The pressure on the abdominal wall 22 is observed within the gastric cavity 10 through the gastroscope 20 to also determine the appropriate placement of one or more trocars (or other ports allowing abdominal access) for completion of the procedure in accordance with the present invention.

After the gastric cavity 10 has been mapped with the aid of the gastroscope 20, a tissue conveyor 24 in accordance with the present invention is inserted transesophageally into the gastric cavity 10. With reference to FIGS. 2 and 8-16, the present tissue conveyor 24 creates a serosa-to-serosa fold 12 from within the gastric cavity 10 for a transoral procedure in the treatment of morbid obesity in gastric volume reduction surgery. As the formation of a serosa-to-serosa fold 12 may be complicated, the present tissue conveyor 24 facilitates an efficient completion of the procedure. The present invention assists in the formation of a serosa-to-serosa fold 12 by drawing tissue into a folded configuration in which it may be secured using suture anchoring devices 26.

More particularly, and with reference to FIGS. 3, 4, 5, 6 and 7, the tissue conveyor 24 includes a conveyor body 25 having a proximal end 28 and a distal end 30. The proximal end 28 is provided with a handle 32 allowing for operator control of an end effector 34 located at the distal end 30 of the tissue conveyor 24. As will be discussed below in greater detail, the handle 32 includes a control wheel 96 actuating movement of first and second conveyor members 62, 64 for pulling tissue into a fold 12 at the end effector 34. In addition, and as will also be appreciated based upon the following disclosure, the handle 32 also includes a lever 98 connected to a linkage assembly 100 for controlling pivotal movement of the first and second jaw bars 40, 42 as they are manipulated to draw tissue into a folded configuration in accordance with the present invention. A flexible tube 36 connects the proximal end 28 of the tissue conveyor 24 to the distal end 30 of the tissue conveyor 24 allowing the tissue conveyor 24 to be inserted transorally for completion of the present procedure with minimal trauma to the patient.

The end effector 34 includes a grasper assembly 38 shaped and dimensioned for engaging tissue in the formation of a serosa-to-serosa fold 12 along the anterior wall 14 of the gastric cavity 10. The grasper assembly 38 includes a first jaw bar 40 and a second jaw bar 42 connected by a support base 44 to define a cavity 102 into which tissue is drawn in accordance with the present invention. The first jaw bar 40 and the second jaw bar 42 are pivotally secured to the support base 44 of the end effector 34 that is directly connected to the flexible tube 36 connecting the proximal end 28 of the tissue conveyor 24 to the distal end 30 of the tissue conveyor 24. As such, the first and second jaw bars 40, 42 are pivotally supported for pivotal movement about an axis that is substantially transverse to the longitudinal axis of the end effector 34. The first jaw bar 40, therefore, pivots about an axis which is substantially parallel to the axis about which the second jaw bar 42 pivots, while the axis about which the first jaw bar 40 pivots and the axis about which the second jaw bar 42 pivots are separated by a distance sufficient to permit the first and second jaw bars 40, 42 to grab tissue therebetween and hold the tissue for fastening in the creation of a serosa-to-serosa fold 12.

The first jaw bar 40 includes a first end 46 and a second end 48. The first end 46 is pivotally connected to the support base 44 as described above and the second end 48 of the first jaw bar 40 is free for movement about an arc. The first jaw bar 40 further includes an internal surface 50 and an external surface 52. Similarly, the second jaw bar 42 includes a first end 54 and a second end 56. The first end 54 is pivotally connected to the support base 44 as described above and the second end 56 of the second jaw bar 42 is free for movement about an arc. The second jaw bar 42 further includes an internal surface 58, which the faces the internal surface 50 of the first jaw bar 40, and an external surface 60. As such, the first jaw bar 40 and the second jaw bar 42 may be selectively moved about their respective arcs for engaging tissue between the respective internal surfaces 50, 58 of the first jaw bar 40 and the second jaw bar 42.

A first conveyor member 62 is positioned upon the first jaw bar 40 for movement along the internal surface 50 of the first jaw bar 40 and a second conveyor member 64 is positioned upon the second jaw bar 42 for movement along the internal surface 58 of the second jaw bar 42. The first and second conveyor members 62, 64 are actuated to facilitate the drawing of tissue within the cavity 102 between the first jaw bar 40 and the second jaw bar 42.

The first conveyor member 62 includes an inner gripping surface 66 and an outer surface 68. The inner gripping surface 66 faces the cavity 102 between the first and second jaw bars 40, 42. The first conveyor member 62 includes a series of thin, v-shaped cutouts 70 along its length. The thin cutouts 70 provide added flexibility to the first conveyor member 62 allowing the first conveyor member 62 to bend around a pulley member 104 at the distal tip 72 at the second end 48 of the first jaw bar 40 as cutouts 70 extend outwardly and engage the tissue bringing it into the cavity 102 between the first and second jaw bars 40, 42.

The second conveyor member 64 also includes an inner gripping surface 67 and an outer surface 69. The inner gripping surface 67 faces the cavity 102 between the first and second jaw bars 40, 42. The second conveyor member 64 includes a series of thin, v-shaped cutouts 71 along its length. The thin cutouts 71 provide added flexibility to the second conveyor member 64 allowing the second conveyor member 64 to bend around a pulley member 106 at the distal tip 73 at the second end 56 of the second jaw bar 42 as cutouts 71 extend outwardly and engage the tissue bringing it into the cavity 102 between the first and second jaw bars 40, 42.

Each of the first and second conveyor members 62, 64 includes a first end 108, 110 and a second end 112, 114. Through a coupling arrangement described below in greater detail, the first and second conveyor members 62, 64 are connected to first and second string members 116, 118 wrapped about the end effector 34 for actuation of the first and second conveyor members 62, 64 in a manner creating simultaneous movement of the first and second conveyor members 62, 64.

In particular, the first end 108 of the first conveyor member 62 is provided with a first sled 120, shaped and dimensioned to move between the first end 46 and the second end 48 of the first jaw bar 40 in a controlled manner, while the second conveyor member 64 is similarly provided with a second sled 122, shaped and dimensioned to move between the first end 54 and the second end 56 of the second jaw bar 42 in a controlled manner sled. The first string member 116 connects the first sled 120 to the second end 114 of the second conveyor member 64 and a second string member 118 connects the second sled 122 to the second end 112 of the first conveyor member 62. The first string member 116 is routed within the tissue conveyor 24 such that it extends from the first sled 120 toward the proximal end 28 of the tissue conveyor 24 and about a control wheel 96 located at the proximal end 28 of the tissue conveyor 24. The first string member 116 then extends toward the distal end 30 of the tissue conveyor 24 along the second jaw bar 42 where it is connected to the second end 114 of the second conveyor member 64. The second string member 118 extends from the second sled 122 toward the second end 56 of the second jaw arm 42 and about the end effector 34 to the first jaw bar 40 where it then extends distally along the first jaw bar 40 where it is connected to the second end 112 of the first conveyor member 62. Passage of the first and second string members 116, 118 within the tissue conveyor 24 is controlled by the inclusion of a series of pulleys positioned to facilitate movement of the of the first and second string members 116, 118 as they extend between the first and second conveyor members 62, 64.

The first and second conveyor members 62, 64 are linked for simultaneous motion as the first string member 116 (and actually the second string member 118) is manipulated by the control wheel 96. As the first string member 116 is manipulated by actuation of the control wheel 96 to pull the first sled 120 back and forth, the first and second conveyor members 62, 64 are drawn into and out of the cavity 102 defined by the first and second jaw bars 40, 42. By drawing the first and second conveyor members 62, 64 into the cavity 102 defined by the first and second jaw bars 40, 42, that is, the first and second conveyor members 62, 64 are pulled toward the second ends 48, 56 of the respective first and second jaw bars 40, 42, tissue is drawn into the cavity 102 defined by the first and second jaw bars 40, 42. As briefly mentioned above, each of the first and second conveyor members 62, 64 is provided with a series of v-shaped cutouts 70, 71. These cutouts 70, 71 create sharp prongs as the respective first and second conveyor members 62, 64 are drawn over and around the pulley members 104, 106 located at the distal tips 72, 73 of the first and second jaw bars 40, 42. The sharp prongs engage the tissue as the first and second conveyor members 62, 64 are drawn into the cavity 102 defined by the first and second jaw bars 40, 42, thereby pulling the tissue into the cavity 102 for folding the tissue in accordance with the present invention.

In practice, and with particular reference to FIGS. 5, 6, 7, 8 and 9, the end effector 34 is oriented with the first and second jaw bars 40, 42 substantially parallel for transoral insertion. Once inserted into the gastric cavity 10, the first and second jaw bars 40, 42 are fully extended outwardly distally extending the flexible material outward. Once the device is fully deployed, the distal tips 72, 73 of the respective first and second jaw bars 40, 42 are pushed into the mucosal layer of the stomach wall in the area where a fold is desired. The first and second conveyor members 62, 64 are then pulled proximally, that is, the control wheel 96 is rotated to cause the first and second string members 116, 118 to act upon the first and second sleds 120, 122 in a manner drawing the first and second conveyor members 62, 64 into the cavity 102 defined by the first and second jaw bars 40, 42. As the first and second conveyor members 62, 64 are drawn proximally within the cavity 102 defined by the first and second jaw bars 40, 42, the first and second conveyor members 62, 64 respectively bend as they move over the pulley members 104, 106 located at the distal tip 72, 73 of the first and second jaw bars 40, 42. This bending allows the flexible v-shaped cutouts 70, 71 to extend outwardly from the surface of the conveyor members in a manner facilitating engagement with tissue while the first and second conveyor members 62, 64 are simultaneous drawn into the cavity 102 defined between the first and second jaw bars 40, 42. As the first and second conveyor members 62, 64 draw the tissue inwardly between the first and second jaw bars 40, 42, the tissue is brought into a nice fold for subsequent tissue fasteners to be applied.

Once the serosa-to-serosa fold is created through the implementation of the present tissue conveyor 24, the tissue must be fastened to hold it in the folded configuration. One such method of fastening after the serosa-to-serosa fold 12 is created is to insert a trocar 94 through the abdominal wall 22 directly above the created serosa-to-serosa fold 12. The trocar 94 preferably has a diameter of between approximately 3 mm and approximately 5 mm to allow an adequate passageway for instruments and suture anchoring devices 26 employed in accordance with the implementation of the techniques described herein.

With the trocar 94 inserted into the abdominal wall 22, a suture anchor deployment device 74 is passed through the trocar 94 into the abdominal cavity 23. Prior to insertion of the deployment device 74, the tip 76 of the deployment device 74 is pressed against the anterior wall 14 of the gastric cavity 10 to indent the wall, as shown in FIG. 10. The indentation along the wall of the gastric cavity 10 is visualized through the gastroscope 20 to determine the proper location to insert the deployment device 74 into the gastric cavity 10. After the proper insertion location is determined, the tip 76 of the deployment device 74 is inserted into the interior of the gastric cavity 10. The deployment device 74 is inserted into the gastric cavity 10 with sufficient force to prevent the deployment device 74 from glancing off of the exterior surface of the anterior wall 14 of the gastric cavity 10. After the tip 76 of the deployment device 74 is inside the gastric cavity 10, as shown in FIG. 11, a suture anchoring device 26 is deployed from the deployment device 74 into the interior of the gastric cavity 10. In the embodiment shown in the various figures, the suture anchoring device 26 is a T-tag fastener. However, other types of tissue fasteners suitable for holding together portions of the gastric cavity wall in the creation of folds may also be used in accordance with the spirit of the present invention. Examples of suitable tissue fasteners include t-type anchors as already discussed, reconfigurable "basket"-type anchors (which generally comprise a number of configurable structure legs extending between at two collars or support members), and linear anchors (elongated anchors which are configured to fold or become compressed in to a bowed or expanded configuration). In general, anchor characteristics are such that prior to deployment, they can easily be placed into or through tissue(s), but after deployment, have an altered configuration providing at least one dimension sufficiently large to maintain the anchor in place.

After the T-tag fastener 26 is deployed into the gastric cavity 10, the deployment device 74 is removed from the gastric cavity 10 as shown in FIG. 12. As the deployment device 74 is removed, the suture material 78 attached at the distal end 80 to the T-tag fastener 26 extends from the T-tag fastener 26 and through the anterior wall 14 of the gastric cavity 10. The proximal end 82 of the suture material 78 extends through the trocar 94 and outside the body.

After the deployment device 74 is removed from the anterior wall 14 of the gastric cavity 10, the anterior wall 14 again is probed with the tip 76 of the deployment device 74 to determine the location for a second T-tag fastener 26. To facilitate the anterior wall 14 probing, the trocar 94 may be flexed at different angles within the abdominal wall 22 as shown in FIG. 13 without removing the trocar 94 from the abdominal wall 22. The trocar 94 is angled within the abdominal wall 22 to enable the deployment device 74 to enter the gastric cavity 10 at different locations and in a different direction roughly perpendicular to the exterior surface of the gastric cavity 10. Once the proper placement location is determined, the deployment device 74 is once again inserted into the gastric cavity 10. With the deployment device 74 inside the gastric cavity 10, a second T-tag fastener 26 is deployed into the interior of the gastric cavity 10. A second length of suture material 78 is attached at a distal end 80 of the second T-tag fastener 26. After the second T-tag fastener 26 is deployed, the deployment device 74 is removed from the gastric cavity 10, drawing the length of suture material 78 back through the anterior wall 14 of the gastric cavity 10. The proximal ends 82 of the first and second lengths of suture material 78 are drawn through the trocar 94 and external of the body. Tension is then applied to the proximal ends 82 of the respective first and second lengths of suture material 78 to draw the fastened portion of the anterior wall 14 of the gastric cavity 10 together to form a serosa-to-serosa fold 12 as shown in FIG. 14. The first and second lengths of suture material 78 are then locked in a tensioned state by applying a knotting element 84 to the proximal ends 82 of the respective first and second lengths of the suture material 78. The knotting element 84 is passed back through the trocar 94 to a location between the abdominal wall 22 and the anterior wall 14 of the gastric cavity 10.

Figure 15:
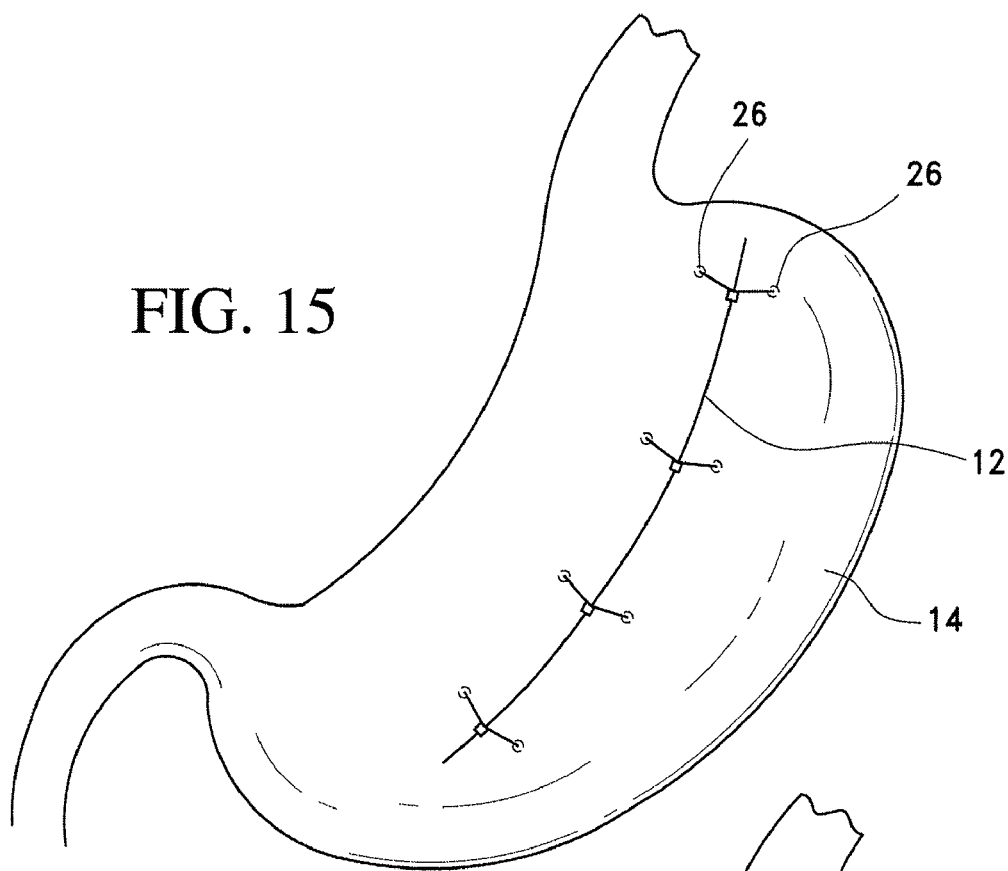
Figure 16:
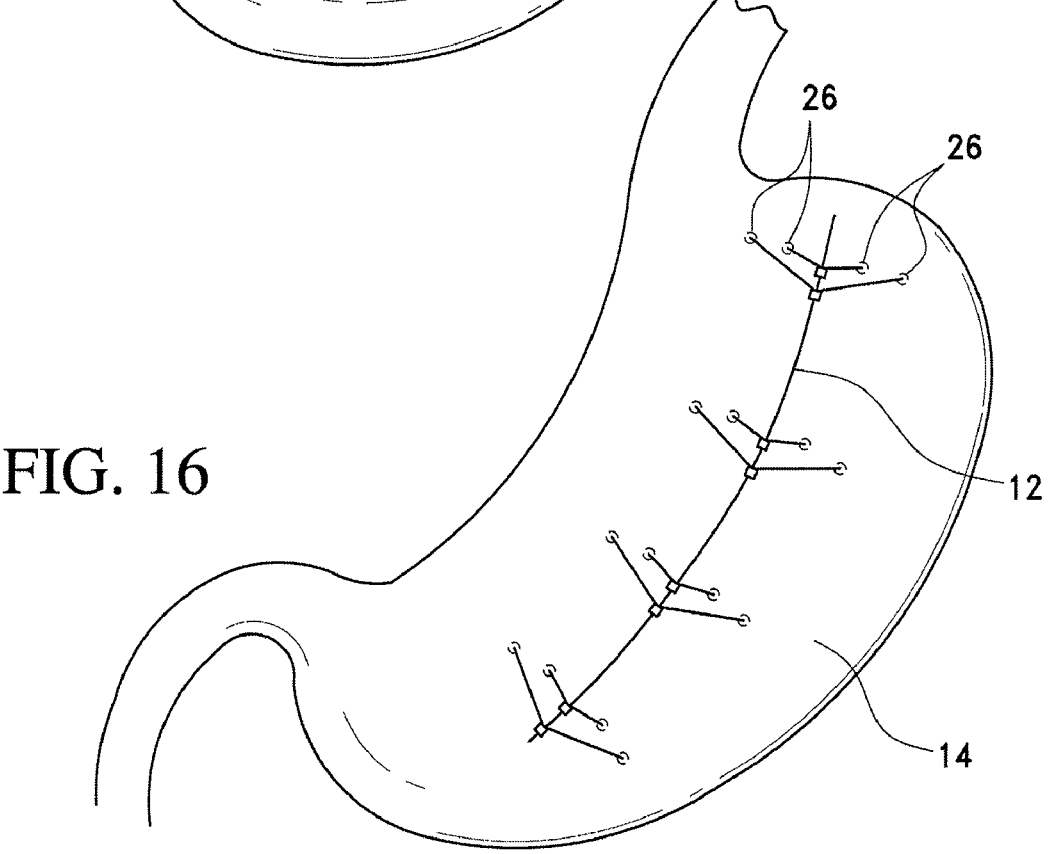

In addition to knotting elements, the suture material may also be locked in a tensioned state by tying a knot in the suture material. The knot may be tied laparoscopically through the trocar. Alternatively, the knot may be tied external of the body, and the finished knot passes back through the trocar to a point between the abdominal wall and the anterior wall of the gastric cavity. In an alternate embodiment, the first and second lengths of suture materials are pre-tied within the deployment device. The suture material may be of a sufficient length that the knot can be externalized from the body through the trocar, or can be short enough that laparoscopic manipulation is required to apply tension between the suture anchoring devices. In yet another embodiment, the suture anchoring devices are connected by a single piece of suture material (not shown) within the length chosen to be easily externalized or short enough to be completely tensioned internally. In either case, the suture material and anchors may be pre-loaded within a deployment device in one or more sets, or can be loaded into cartridges that can be reloaded as needed. FIG. 15 shows an external view of the gastric cavity with the suture anchoring devices and the suture material cinched between the suture anchoring devices to maintain the serosa-to-serosa fold therebetween. The knotting element is shown applied to the suture material to lock the tension in the suture material.

After the first pair of T-tag fasteners is deployed, the tissue conveyor is removed from engagement with the tissue and moved to another location spaced down from the length of the anterior wall from the first pair of suture anchoring devices. Thereafter the procedure is repeated to form an additional fold with the tissue conveyor and the fold is secured in the manner described above. Additional folds may then be created along the length of the wall of the gastric cavity and additional pairs of suture anchoring devices may be deployed along the longitudinal length of the anterior wall of the gastric cavity to hold the fold in a secure configuration.

After an initial series of suture anchoring device pairs are deployed into the anterior wall of the gastric cavity and cinched together to hold the serosa-to-serosa fold in a securely held configuration, it may still be desirable to create a deeper fold. As such, a deeper fold may be created using the present tissue conveyor and a second series of suture anchoring device pairs may be deployed to increase the depth of the fold (see FIG. 16).

Following deployment of the second series of suture anchoring devices, additional series of suture anchoring devices may be deployed to further increase the depth of the fold, depending upon the desired stomach volume reduction. Additionally, the fold may be further reinforced by applying fastening devices including anchors, staples, etc. to the internal side of the anterior wall of the gastric cavity and/or through the fold. This is preferably performed endoscopically with an endoscopic instrument (stapler, suturing device, suture anchor deployment device, etc.), but may also be performed laparoscopically, preferably through the existing trocar(s).

As an alternative to the embodiment described above, suture anchoring devices may be passed through the gastroscope into the gastric cavity. An instrument may be passed on the end of or through the gastroscope for attaching the suture anchoring devices into one of the gastric cavity walls to form a fold. Suture material may be tensioned adjacent to or through the gastroscope, and a knotting element passed adjacent to or through the gastroscope to the fold, to lock in the suture tension. Suture anchoring devices may also be passed into the gastric cavity adjacent to or through the gastroscope and attached to the anterior wall of the gastric cavity through a laparoscope.

Figure 17:
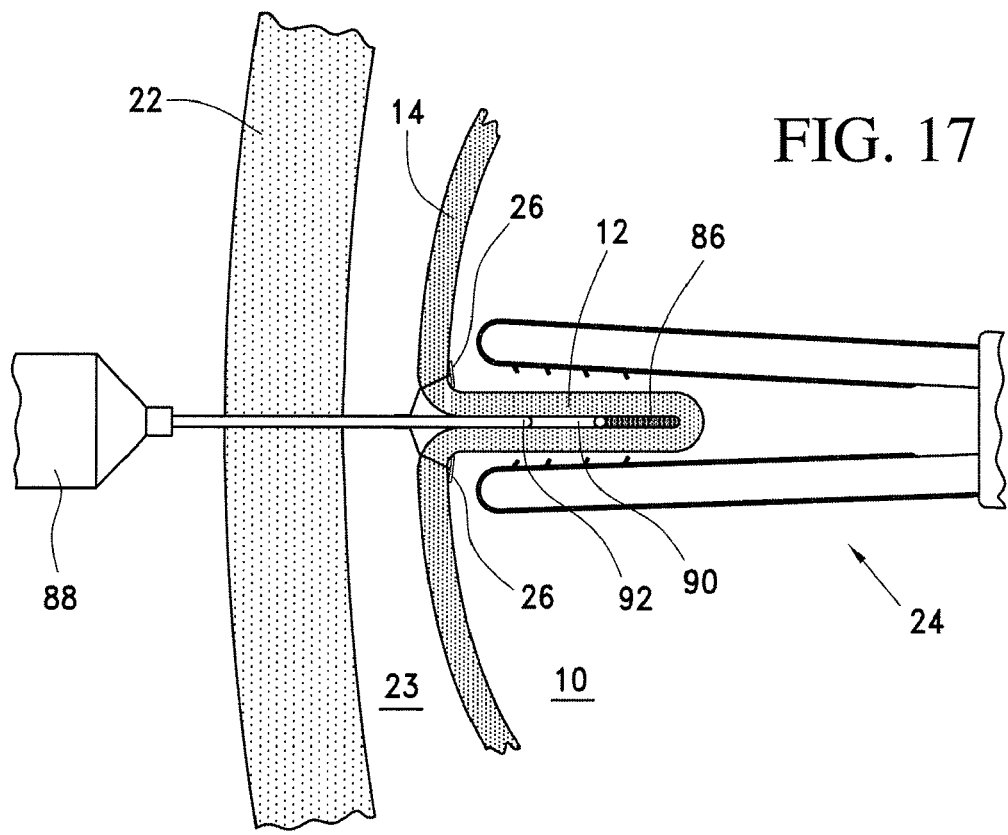
FIGS. 17 and 18 show application of adhesive to a fold created in accordance with the present invention.
Figure 18:
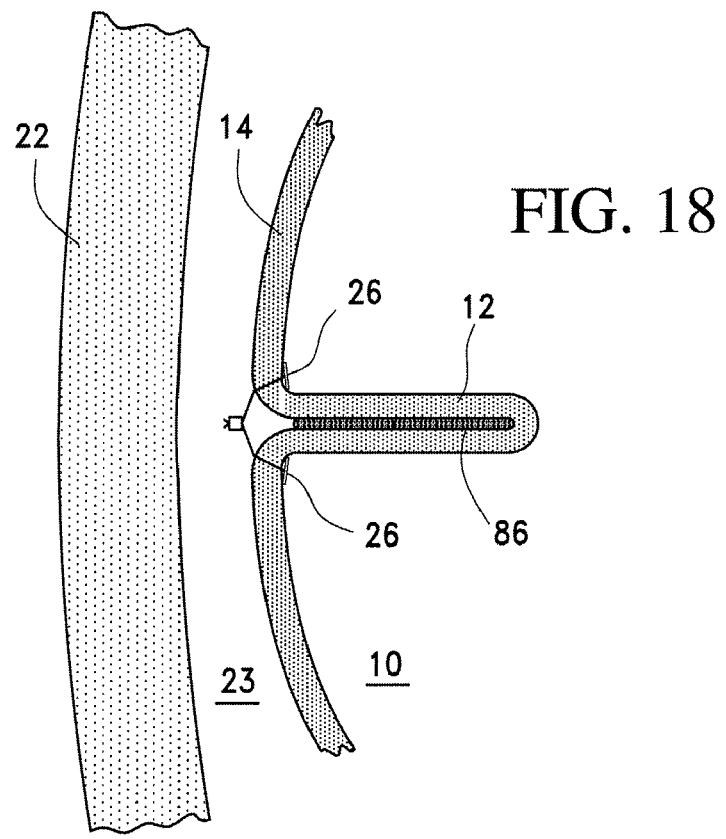

In addition to fastening a serosa-to-serosa fold 12 using mechanical fasteners 26, it is contemplated that biosurgical adhesives 86 may be applied to the tissue and utilized in the gastroplasty procedure to hold the serosa-to-serosa fold 12 in a desired configuration. In accordance with this embodiment, and with reference to FIGS. 17 and 18, a biosurgical adhesive 86 is injected from outside the body into the fold 12 created along the external surface of the gastric cavity 10 as the fold 12 is held utilizing a fold forming apparatus, for example, the present tissue conveyor 24. In accordance with a preferred embodiment, the adhesive dispenser 88 may be a tubular injection needle 90 with an articulation joint 92 provided.

Utilization of an articulated joint 92 provides for the passage of a large amount of adhesive 86 to be delivered to the desired site. Other examples of fold forming apparatus, which may be used in conjunction with the present techniques described herein are described in commonly owned and pending U.S. patent application Ser. No. 11/696,217, filed Apr. 4, 2007, pending U.S. patent application Ser. No. 11/696,221, filed Apr. 4, 2007, pending U.S. patent application Ser. No. 11/696,222, filed Apr. 4, 2007, pending U.S. patent application Ser. No. 11/696,225, filed Apr. 4, 2007, pending U.S. patent application Ser. No. 11/696,228, filed Apr. 4, 2007, and pending U.S. patent application Ser. No. 11/696,231, filed Apr. 4, 2007, which are hereby incorporated herein by reference in their entirety.

In accordance with an alternate embodiment, and with reference to FIGS. 19 and 20, the tubular injection needle 190 for the adhesive 186 is provided with an articulating joint 194. The use of an articulating joint 194 along the length of the tubular injection needle 190 is believed to provide a passageway for a large amount of adhesive 186 to the treatment site. In particular, by orienting a portion of the tubular injection needle 190 transverse to the remainder of the injection needle 190, the injection needle may be used to push inwardly along the fold to assist in the formation of the fold.

Referring to FIG. 21, it is further contemplated that tissue fasteners, such as, T-tag fasteners, 26 may be utilized in conjunction with the surgical adhesive 86 to enhance the securing effect. When utilizing such a procedure, the dispensing needle 90 may be moved in and out of the fold 12 location until all tissue is coated with the surgical adhesive 86. In addition to applying surgical adhesive 86 to the fold from external to the stomach, an endoscope 93 may be utilized to incorporate the adhesive into the serosa-to-serosa fold 12. Utilizing such an embodiment, the endoscope 93 would be passed transorally into the stomach. Thereafter, an aperture would be formed within the stomach for accessing the external surface of the stomach located within the serosa-to-serosa fold 12. Thereafter, the endoscope 93 would be forced through the aperture and into the recess of the serosa-to-serosa fold 12. The adhesive would then be applied to the area within the fold.

In accordance with another embodiment, it is contemplated the adhesive may be administered through the present tissue conveyor. In accordance with such and embodiment, the tissue conveyor would be provided with a needle through a central aspect of the device, so that either before or (preferably) after the tissue has been plicated, a needle is extended from the tissue conveyor, through the tissue, and into the region between the serosa-to-serosa contact. Once in this region, the adhesive is dispensed from through the needle.

While adhesive and anchors are described above in securing a fold formed in accordance with the present invention, those skilled in the art will appreciate other attachment techniques may be employed. For example, the preceding disclosure describes a "hybrid approach" where an abdominal access port is needed to secure the fold. It is contemplated, the fold could also be secured in a fully trans-oral approach where a t-tag fastener is used within the present device, or alongside the present device, (that is, the present conveyor device would be integrated with a fastener deployment device for securing the tissue as soon as it is folded in accordance with the present invention. It is also contemplated a T-tag fastener type device could be actuated and utilized through the working channel of a flexible endoscope.

Although T-tag fasteners are disclosed for use in accordance with various embodiments disclosed herein, various other tissue fasteners which are suitable for apposing and securing tissue such as, for example, simple suture knots and laparoscopically deployable suture anchors, may also be utilized without departing from the scope of the invention. As one skilled in the art will recognize, examples of fasteners suitable for this task include but are not limited to the T-type anchors (mentioned above and described in more detail below), reconfigurable "basket"-type anchors (which generally comprise a number of configurable struts or legs extending between two collars or support members), and linear anchors (elongate anchors which are configured to fold or become compressed into a bowed or expanded configuration). In general, anchor characteristics are such that prior to deployment they can easily be placed into or through tissue(s), but after deployment, have an altered configuration providing at least one dimension sufficiently large to maintain the anchor in place.

While the first and second jaw bars are disclosed herein as being pivotally mounted, it is contemplated they may be fixed mounted upon the support base without departing from the spirit of the present invention.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used system is obtained and if necessary cleaned. The system can then be sterilized. In one sterilization technique, the system is placed in a closed and sealed container, such as a plastic or TYVEK bag. The container and system are then placed in a field of radiation that can penetrate the container, such as gamma radiation, x-rays, or high-energy electrons. The radiation kills bacteria on the system and in the container. The sterilized system can then be stored in the sterile container. The sealed container keeps the system sterile until it is opened in the medical facility.

It is preferred that the device is sterilized. This can be done by any number of ways known to those skilled in the art including beta or gamma radiation, ethylene oxide, and/or steam.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A method for creating a tissue fold, comprising:
    positioning a tissue conveyor adjacent tissue, wherein the tissue conveyor includes a conveyor body including a proximal end and a distal end, the proximal end includes a handle allowing for operator control of an end effector located at the distal end, the end effector includes a grasper assembly composed of a first jaw bar and a second jaw bar connected by a support base to define a cavity into which tissue is drawn, and a first conveyor member is positioned upon the first jaw bar for movement along an internal surface of the first jaw bar and a second conveyor member is positioned upon the second jaw bar for movement along an internal surface of the second jaw bar;
    pushing the respective first jaw bar and the second jaw bar into the tissue in an area where a fold is desired;
    pulling the first conveyor member and the second conveyor member proximally to draw the first and second conveyor members and tissue into a cavity defined by the first jaw bar and the second jaw bar to create a tissue fold.

2. The method according to claim 1, wherein the first jaw bar and the second jaw bar are pivotally secured to the support base of the end effector.

3. The method according to claim 2, wherein the first jaw bar pivots about an axis which is substantially parallel to an axis about which the second jaw bar pivots, while the axis about which the first jaw bar pivots and the axis about which the second jaw bar pivots are separated by a distance sufficient to permit the first jaw bar and the second jaw bar to grab and hold tissue therebetween.

4. The method according to claim 2, wherein the handle includes a lever connected to a linkage assembly for controlling pivotal movement of the first and second jaw bars.

5. The method according to claim 1, wherein the handle includes a control wheel actuating movement of first and second conveyor members for pulling tissue into a fold at the end effector.

6. The method according to claim 1, wherein the first conveyor member includes an inner gripping surface and an outer surface, the inner gripping surface faces a cavity between the first jaw bar and the second jaw bar and the second conveyor member includes an inner gripping surface and an outer surface, the inner gripping surface faces a cavity between the first jaw bar and the second jaw bar.

7. The method according to claim 6, wherein the first conveyor member includes a series of thin, v-shaped cutouts along its length and the second conveyor member includes a series of thin, v-shaped cutouts along its length.

8. The method according to claim 2, wherein the each of the first conveyor member and the second conveyor member includes a first end and a second end, and the first conveyor member and the second conveyor member are connected to first and second string members wrapped about the end effector for actuation of the first conveyor member and the second conveyor members.

9. The method according to claim 8, wherein the first and second string members are wrapped about the end effector for actuation of the first conveyor member and the second conveyor member in a manner creating simultaneous movement of the first conveyor member and the second conveyor member.

10. The method according to claim 1, further including the step of applying a biosurgical adhesive for fastening the tissue fold.

* * * * *